US008463390B2

(12) United States Patent
Muraoka

(10) Patent No.: US 8,463,390 B2
(45) Date of Patent: Jun. 11, 2013

(54) ELECTROSTIMULATOR CAPABLE OF OUTPUTTING STABLE ELECTRIC STIMULUS

(75) Inventor: Yoshihiro Muraoka, Tokorozawa (JP)

(73) Assignee: Health Science Technology Transfer Center Japan Health Sciences Foundation, Tokyo (JP)

(*) Notice: Subject to any disclaimer, the term of this patent is extended or adjusted under 35 U.S.C. 154(b) by 0 days.

(21) Appl. No.: 13/463,101

(22) Filed: May 3, 2012

(65) Prior Publication Data

US 2012/0239112 A1    Sep. 20, 2012

Related U.S. Application Data

(63) Continuation of application No. PCT/JP2010/006408, filed on Oct. 29, 2010.

(30) Foreign Application Priority Data

Nov. 6, 2009  (JP) ................. 2009-254973

(51) Int. Cl.
*A61N 1/00*    (2006.01)

(52) U.S. Cl.
USPC .................. 607/49; 607/48; 607/62

(58) Field of Classification Search
USPC ............................. 607/48, 49, 62
See application file for complete search history.

(56) References Cited

FOREIGN PATENT DOCUMENTS

| JP | 2002-331007 A | 11/2002 |
|---|---|---|
| JP | 2003-241868 A | 8/2003 |
| JP | 2003-310768 A | 11/2003 |
| JP | 2003-310770 A | 11/2003 |
| JP | 3496044 B2 | 2/2004 |
| JP | 2004-255104 A | 9/2004 |

OTHER PUBLICATIONS

International Search Report (ISR) dated Nov. 30, 2010 (in English) issued in counterpart International Application No. PCT/JP2010/006408.
Y. Muraoka et al; EMG-Controlled Hand Opening System for Hemiplegia. Proc. 6th Vienna Int. Workshop on Functional Electrostimulation Basics Technology Appln; pp. 255-258; 1998.
International Search Report and Written Opinion dated Nov. 30, 2010 in counterpart International Application No. PCT/JP2010/006408.

*Primary Examiner* — Niketa Patel
*Assistant Examiner* — Mallika D Fairchild
(74) *Attorney, Agent, or Firm* — Holtz, Holtz, Goodman & Chick, P.C.

(57) ABSTRACT

An electrostimulator includes a boost circuit supplying a stimulus signal, first and second electrodes disposed on a skin surface, detecting a voluntary myoelectric signal and giving the stimulus signal, an amplification circuit amplifying the voluntary myoelectric signal, a controller controlling the stimulus signal in accordance with the voluntary myoelectric signal, an H-bridge circuit including first and third switches connected in series and connected to the second electrode, and second and fourth switches connected in series and connected to the first electrode, the first to the fourth switches being connected in parallel, an isolated DC-DC converter supplying a power to the controller and the amplification circuit, a regulator outputting a midpoint voltage of a power-supply voltage, and a third electrode connected to the regulator and a reference terminal of the amplification circuit and disposed on the skin surface.

13 Claims, 8 Drawing Sheets

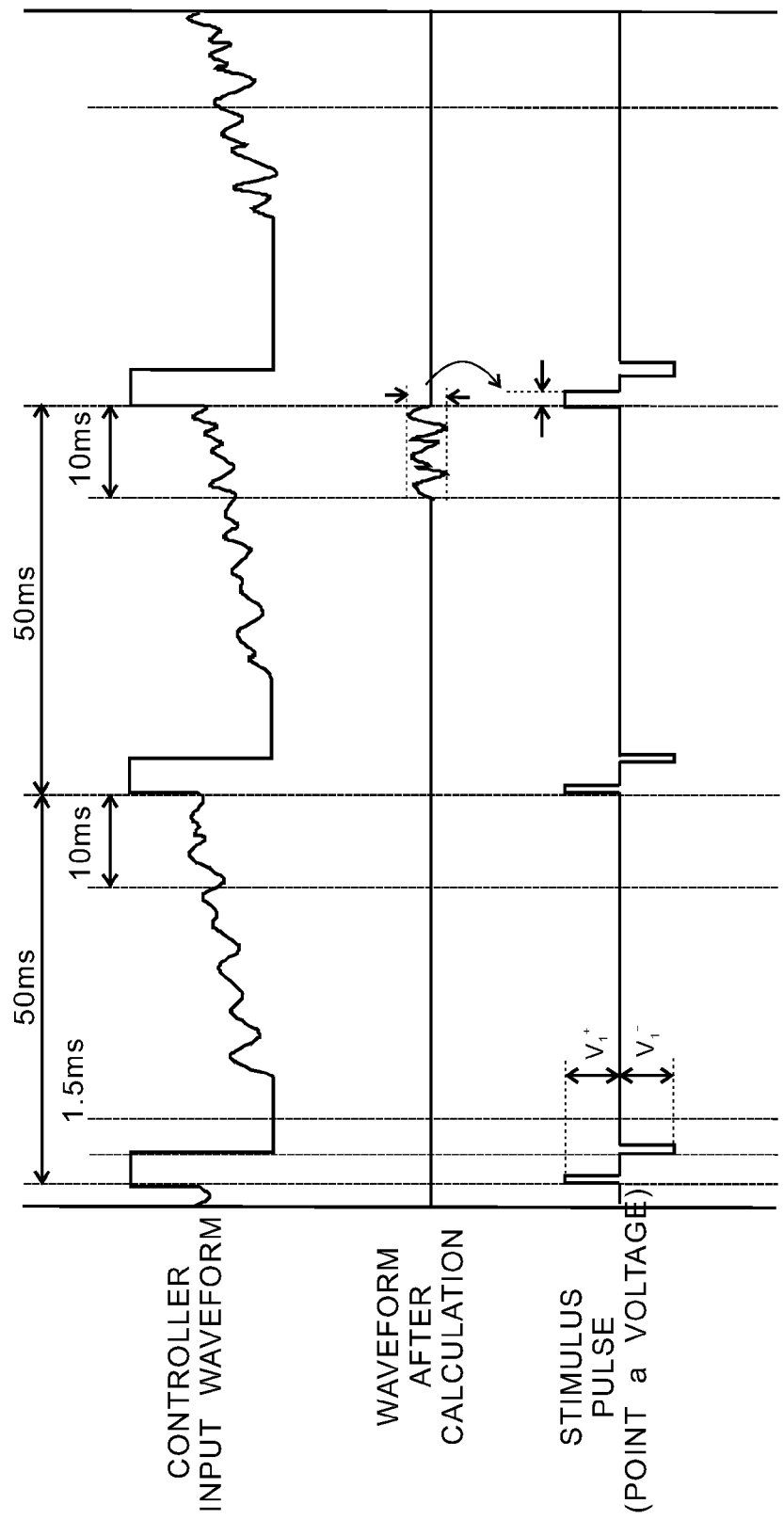

ELECTROSTIMULATOR CAPABLE OF OUTPUTTING STABLE ELECTRIC STIMULUS

This application is based on Japanese Patent Application 2009-254973, filed on Nov. 6, 2009, and International Application PCT/JP2010/006408, filed on Oct. 29, 2010, the entire contents of which are incorporated herein by reference.

BACKGROUND OF THE INVENTION

A) Field of the Invention

This invention relates to an electrostimulator, and more specifically relates to an electro stimulator which is ideal for assisting or recovering motor functions or strengthening of muscular power of a patient who has had a cerebrovascular accident or the like.

B) Description of the Related Art

There is known "drop-foot" as a sequela of hemiplegia caused by a cerebrovascular accident. Dorsiflexion of an ankle joint is difficult for a patient with drop-foot because of a weakness in the dorsiflexion muscle group and hyperfunction of the plantarflexion muscle group. Therefore, in swing phase of walking, a healthy person can smoothly move a foot forward by dorsiflexion of an ankle joint by contraction of the dorsiflexion muscle group. On the other hand, in case of a patient with drop-foot, a toe touches the ground because of no dorsiflexion of an ankle joint. By this "shuffling gait", walking becomes hard for a patient with drop-foot.

FIG. 8 is a circuit diagram showing a structure of an electrostimulator according to a first prior art. This structure is disclosed by Japanese Laid-Open Patent No. 2002-331007 (Patent Document 1), and before that, the inventor of the present invention published the first prior art in Muraoka, Y., et. al., EMG-controlled hand opening system for hemiplegia. Proc. 6th Vienna International Workshop on Functional Electrostimulation Basics Technology Application: pp. 255-258, 1998 (Non-Patent Document 1).

Electrodes E11 and E12 are disposed on a muscle belly of muscle from which a muscle activity is picked-up, and an electrode E3 is disposed on an arbitrary position. Even in case of a patient, a faint voluntary myoelectric signal (or electromyography (EMG) signal) is output when the patient tries to contract the muscle, and so the electrodes E11 and E12 are used for detecting the microscopic voluntary myoelectric signal.

With the electrode E3 as a ground electrode, the voluntary myoelectric signal of the target muscle detected by the electrodes E11 and E12 is input to an instrumentation amplifier 11 via protective resistors R11 and R12.

The input of the instrumentation amplifier 11 is limited to about ±0.5V by the diodes D11 and D12 in order not to saturate the instrumentation amplifier 11. Thereafter the output of the instrumentation amplifier 11 is amplified by a multistage amplifier 12 of several stages with a bandwidth of 300-450 Hz to a level which be recognized by a controller 73, and then the amplified signal is taken at a sampling frequency of 1 kHz from an A/D conversion input PIN of the controller 73.

The controller 73 controls a stimulator (stimulus outputting transformer) 74 by outputting a pulse with a width in proportion to amplitude of the voluntary myoelectric signal. A stimulus pulse is a bipolar pulse, and amplitudes of a positive pulse and a negative pulse are the same. The amplitude of the stimulus pulse is about 100V, and the width of the pulse is adjusted to 50 μs-1 ms. The stimulus becomes stronger as the width becomes wider. A cycle of the stimulus pulse is 50 ms, and photoMOS relays SW11 and SW12 are turned on at the timing when the stimulus pulse is applied and conduct the stimulus pulse to the electrodes E11 and E12. When the stimulus pulse is not applied, the photoMOS relays SW11 and SW12 are turned off in order to prevent mixing of noise from the stimulator (stimulus outputting transformer) 74 and simultaneously prevent a short-circuit between the electrodes E11 and E12 via the transformer.

Moreover, the controller 73 controls the timings of turning on and off of the photoMOS relays SW11 and SW12. This prior art uses a transformer as the stimulator (stimulus outputting transformer) 74 which realizes the amplitude of 100V and isolation simultaneously.

FIG. 9 is a circuit diagram showing a structure of an electrostimulator according to a second prior art. This structure is also disclosed by the inventor of the present invention in the Patent Document 2 (Japanese Laid-Open Patent No. 2003-310768). It is different form the first prior art in that electrodes E14 and E15 are commonly connected to one terminal of a stimulator (stimulus outputting transformer) 74 via diode AC switches (diac) D13 and D14 instead of using the photoMOS relays SW11 and SW12, and another terminal of the stimulator (stimulus outputting transformer) 74 is connected to ground, that is, an electrode E16.

By that, the stimulation is performed by two channels of the electrodes E14 and E15 and the electrode E16, and the measurement of the myoelectric signal is performed by one channel of the electrodes E14 and E15. This prior art also uses a transformer as the stimulator (stimulus outputting transformer) 74.

FIG. 10 is a circuit diagram showing a structure of an electrostimulator according to a third prior art. This structure is also disclosed by the inventor of the present invention in the Patent Document 3 (Japanese Laid-Open Patent No. 2004-255104). It is different form the first and the second prior arts in that a boost circuit without a transformer and an H-bridge circuit are used instead of using the stimulator (stimulus outputting transformer) 74 and the photoMOS relays SW11 and SW12 according to the first prior art for down-sizing and weight reduction, and a capacitor C and photoMOS relays SW5 and SW6 are added to share a power source between the boost circuit and the myoelectric signal measurement system.

The third prior art is operated as follows. The capacitor C is charged when no stimulation is given by turning on the photoMOS relays SW5 and SW6. When the stimulation is given, first the photoMOS relays SW5 and SW6 are turned off not to apply the stimulus to the electrode E3, and the electrode E1 which is negative polarity is excited by flowing electricity from the electrode E2 to the electrode E1 by turning on the photoMOS relays SW1 and SW4 while turning off the photoMOS relays SW2 and SW3. Next, the photoMOS relays SW1 and SW4 are turned off and the electrode E2 which is negative polarity is excited by flowing electricity from the electrode E1 to the electrode E2 by turning on the photoMOS relays SW2 and SW3.

FIG. 11 is a circuit diagram showing a structure of an electrostimulator according to a first comparative example. It is different from the third prior art in that the electrodes E1 and E2 just function as recording electrodes, and electrodes E4 and E5 are added as stimulating electrodes. The stimulus is applied to the electrode E3 unless the photoMOS relays SW5 and SW6 are turned off while the stimulus is given also in this structure, and so the above-described technique effectively works.

FIG. 12 is a waveform diagram for explaining a signal process of a controller for detecting a voluntary myoelectric signal while removing stimulus artifact and evoked myoelectric signals. The bottom line represents the stimulus pulse signal consisting of stimulus pulse waveforms impressed every 60 ms. One unit of stimulus pulse signal consists of two stimulus pulse waveforms which are the same stimulus pulse waveforms. Therefore, the stimulus waveforms are renewed every 120 ms.

At an input of the controller 13, a voluntary myoelectric signal is input to the A/D conversion input PIN, sampled at a sampling cycle of 1 ms and converted to a digital signal. The waveform, as shown in the second line from the bottom, is a signal formed by convolving the myoelectric signal including an M-wave with the stimulus signal and the artifact.

The stimulus signal is input at the beginning of the 60 ms cycle. The amplitude of the signal is extremely large comparing to the voluntary myoelectric signal, and the stimulus signal is not necessary for the following signal processes; therefore, the amplitude of the signal is limited not to exceed a predetermined level by two diacs.

Two stimulus waveforms at 60 ms cycle are the same so that the corresponding two artifacts and the M-waves are also the same. Therefore, only the voluntary myoelectric signal can be extracted by cancelling the artifacts and the M-waves out. The signals are not stable from the beginning of the 60 ms cycle for a while (approximately 20 ms); therefore, it becomes possible to extract the component of the voluntary myoelectric signal stably by taking the difference near the end of the cycle (the difference is taken in 15 ms before the end in the below-described example but may be taken in a longer period).

LIST OF RELATED PRIOR ART DOCUMENTS

Patent Documents

Patent Document 1: Japanese Laid-Open Patent No. 2002-331007
Patent Document 2: Japanese Laid-Open Patent No, 2003-310768
Patent Document 3: Japanese Laid-Open Patent No. 2004-255104
Patent Document 4: Japanese Patent No. 3496044

Non Patent Document

Non Patent Document 1: Muraoka, Y., et. al., EMG-controlled hand opening system for hemiplegia. Proc. 6th Vienna International Workshop on Functional Electrostimulation Basics Technology Application: pp. 255-258, 1998.

In the above-described prior art, it is preferable to use a capacitor C with a maximum rated voltage of 100V or more and to be as small as possible for miniaturization but a capacitor under that condition has a capacity of several μF. Therefore, electrical potential cannot be sufficiently stored and, according to the prior arts, charging of electricity is stopped during the stimulation so that the charging becomes insufficient when the stimulus is continuously output, an output voltage decreases, and the stimulus becomes unstable.

Moreover, a positive power source and a negative power source are necessary for an amplifier although a circuit has been miniaturized, and if the positive power source is shared with a boost circuit, two or more batteries are necessary.

Furthermore, the above-described signal process can extract a voluntary myoelectric signal; however, the stimulus pulses are renewed every 120 ms and so the maximum delay of 120 ms may be produced from the generation of muscle contraction to the renewal of the stimulus pulses. Therefore, the stimulus sometimes cannot follow a walking activity at a time of fast walking.

SUMMARY OF THE INVENTION

It is an object of the present invention to provide an electrostimulator capable of outputting a stable electric stimulus and detecting a stable voluntary myoelectric potential.

According to one aspect of the present invention, there is provided an electrostimulator, comprising: a boost circuit with no transformer, which receives power supply from a battery and supplies a stimulus signal; a first electrode and a second electrode which are disposed on a skin surface, detect a voluntary myoelectric signal, and give the stimulus signal supplied from the boost circuit; an amplification circuit which amplifies the detected voluntary myoelectric signal; a controller which controls the stimulus signal in accordance with the voluntary myoelectric signal detected by the first and the second electrodes; an H-bridge circuit which comprises a first switch and a third switch that are connected in series while a common connection terminal thereof is connected to the second electrode, and a second switch and a fourth switch that are connected in series while a common connection terminal thereof is connected to the first electrode, the first switch, the second switch, the third switch and the fourth switch being connected in parallel, the H-bridge circuit being controlled by the controller; an isolated DC-DC converter which receives the power supply from the battery and supplies a power to the controller and the amplification circuit; a regulator which outputs a midpoint voltage of a power-supply voltage outputted by the DC-DC converter; and a third electrode which is connected to the regulator and a reference terminal of the amplification circuit and disposed on the skin surface.

According to another aspect of the present invention, there is provided an electrostimulator, comprising: a boost circuit with no transformer, which receives power supply from a battery and supplies a stimulus signal; a first electrode and a second electrode which are disposed on a skin surface and detect a voluntary myoelectric signal; an amplification circuit which amplifies the detected voluntary myoelectric signal; a fourth electrode and a fifth electrode which are disposed on a skin surface and give the stimulus signal supplied from the boost circuit; a controller which controls the stimulus signal in accordance with the voluntary myoelectric signal detected by the first and the second electrodes; an H-bridge circuit which comprises a first switch and a third switch that are connected in series while a common connection terminal thereof is connected to the fourth electrode, and a second switch and a fourth switch that are connected in series while a common connection terminal thereof is connected to the fifth electrode, the first switch, the second switch, the third switch and the fourth switch being connected in parallel, the H-bridge circuit being controlled by the controller; an isolated DC-DC converter which receives the power supply from the battery and supplies a power to the controller and the amplification circuit; a regulator which outputs a midpoint voltage of a power-supply voltage outputted by the DC-DC converter; and a third electrode which is connected to the regulator and a reference terminal of the amplification circuit and disposed on the skin surface.

According to further aspect of the present invention, there is provided an electrostimulator, comprising: a boost circuit with no transformer, which receives power supply from a battery and supplies a stimulus signal; a first electrode and a second electrode which are disposed on a skin surface, detect a voluntary myoelectric signal, and give the stimulus signal supplied from the boost circuit; an amplification circuit which amplifies the detected voluntary myoelectric signal; a controller which controls the stimulus signal in accordance with the voluntary myoelectric signal detected by the first and the second electrodes; an H-bridge circuit which comprises a first switch and a third switch that are connected in series while a common connection terminal thereof is connected to the second electrode, and a second switch and a fourth switch that are connected in series while a common connection terminal thereof is connected to the first electrode, the first switch, the second switch, the third switch and the fourth switch being connected in parallel, the H-bridge circuit being controlled by the controller; a fifth switch which is connected between the common connection terminal of the second and the fourth switches and the first electrode; a sixth switch which is connected between the common connection terminal of the second and the fourth switches and the second electrode; an isolated DC-DC converter which receives the power supply from the battery and supplies a power to the controller and the amplification circuit; a regulator which outputs a midpoint voltage of a power-supply voltage outputted by the DC-DC converter; and a third electrode which is connected to the common connection terminal of the first and the third switches, the regulator and a reference terminal of the amplification circuit and disposed on the skin surface.

According to the present invention there is provided an electrostimulator capable of outputting a stable electric stimulus and detecting a stable voluntary myoelectric potential.

BRIEF DESCRIPTION OF THE DRAWINGS

FIG. 12 is a waveform diagram for explaining a signal process of a controller for detecting a voluntary myoelectric signal while removing stimulus artifact and evoked myoelectric signals.

DESCRIPTION OF THE PREFERRED EMBODIMENTS

Figure 1:
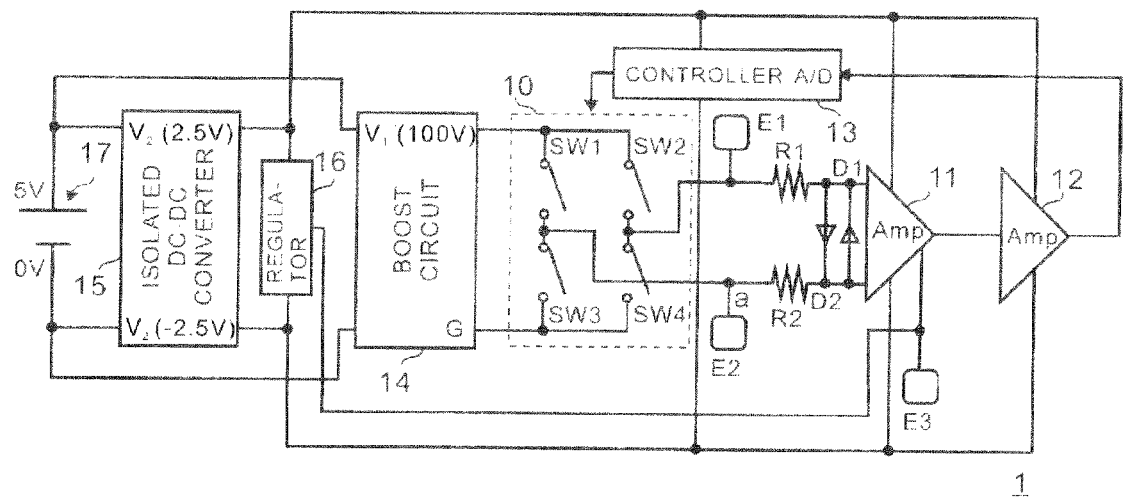
FIG. 1 is a circuit diagram showing a structure of an electrostimulator 1 according to a first embodiment of the present invention.

FIG. 1 is a circuit diagram showing a structure of an electrostimulator 1 according to a first embodiment of the present invention.

The electrostimulator 1 mainly consists of an isolated DC-DC converter 15, electrodes E1, E2 and E3, protective resistors R1 and R2, diodes D1 and D2, an instrumentation amplifier 11, a multi-step amplifier 12, a controller 13, a boost circuit (step-up circuit) 14, an H-bridge circuit 10 and a regulator 16.

A high voltage (100V) is obtained by boosting an output of a battery (5V) 17, and simultaneously the battery (5V) 17 supplies power to the amplifiers 11 and 12 and the controller 13 via the isolated DC-DC converter 15. Moreover, a reference voltage is generated by the regulator 16.

In this embodiment, My Battery Lite manufactured by Japan Trust Technology, INC. is used as the battery 17. The battery 17 is not limited to that product but various types of batteries such as an external battery used for a mobile phone can be used. The electrostimulator 1 can be driven by using only one battery such as an external battery used for a mobile phone which can be obtained easily. Moreover, the battery is not limited to 5V although it is used in the embodiment.

The battery 17 supplying a power to the boost circuit 14 is also connected in parallel to the isolated DC-DC converter 15, and an output of the isolated DC-DC converter 15 forms a power source of about ±2.5V and supplies the power to the amplifiers 11 and 12 and the controller 13.

Moreover, the isolated DC-DC converter 15 of several volts is thin and small and can be obtained easily. In this embodiment, SUS1R50505 manufactured by Cosel Co., Ltd. is used as the DC-DC converter 15. Furthermore, NMA0505D (manufactured by C&D Technologies, Inc.), NKE0505SC (manufactured by Murata Power Solutions), etc. can be used.

By supplying the power to the amplifiers 11 and 12 and the controller 13 via the isolated DC-DC converter 15, a boost circuit system and a myoelectric signal measurement system are isolated.

The regulator 16 generates a mid-point voltage (0V) of the output (about ±2.5V) of the isolated DC-DC converter 15 and is connected to reference terminals of the electrode E3 and the amplifier 11. With this structure, the electrode E3 is not electrically affected by the boost circuit system consisting of the boost circuit 14, etc. Therefore, it can prevent generation of stimulus between the electrodes E1 and E3 or between the electrodes E2 and E3.

The regulator 16 is, for example, formed by connecting two resistors serially and consisting of a voltage dividing circuit that outputs the mid-point voltage (0V) of $V^+_2$ (2.5V) and $V^-_2$ (−2.5V) and a regulator what outputs $(V^+_2 - V^-_2)/2$. Moreover, for example, a half of power source voltage of the amplifier may be generated by a regulator, by a Zener diode or by a resistor divider and a buffer amplifier.

Figure 2:
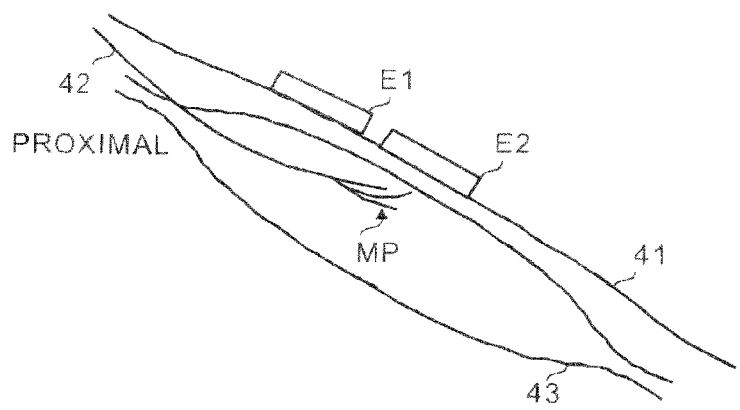
FIG. 2 is a schematic diagram showing disposed positions of stimulus/recording electrodes.

FIG. 2 is a schematic diagram showing disposed positions of stimulus/recording electrodes. One electrode E2 is disposed on a neuromuscular junction MP, and another electrode E1 is disposed on a proximal side position that is several centimeters away from the electrode E2. That is, the electrodes E1 and E2 are disposed on a skin surface 41 of a muscle belly of a muscle 43 from which a muscle action is picked-up, detect a microscopic voluntary myoelectric signal (or electromyography (EMG) signal) generated when a patient tries to move the muscle 43, and function as electrodes for giving stimulus signals to the muscle 43 from the skin 41, Moreover, the electrode E3 is disposed on an arbitrary position on the skin surface 41 and functions as a ground electrode. In order to efficiently promote dorsiflexion of an ankle joint of a patient with drop-foot or the likes like, it is preferable to give stimulus also to fibular nerve exceptionally.

For example, the electrodes E1 and E2 are disposed on a tibialis anterior muscle that lifts up a toe and on a fibular nerve to promote efficient dorsiflexion of an ankle joint in correspondence with moving a foot forward. Moreover, in case of assisting extension of fingers, the electrodes E1 and E2 are disposed on an extensor digitorum muscle of a forearm to promote an action of opening a hand in accordance with an intension of a patient.

Referring to FIG. 1 again, the protective resistors R1 and R2 are connected between the electrodes E1 and E2 and the instrumentation amplifier 11 respectively and protect the instrumentation amplifier 11 at the time of applying the stimulus signals to the electrodes E1 and E2.

The diodes D1 and D2 are connected between input terminals of the instrumentation amplifier 11 in reversed polarities and limit the inputs to about ±0.5V not to saturate the instrumentation amplifier 11.

The instrumentation amplifier 11 receives the voluntary myoelectric signal detected by the electrodes E1 and E2 via the protective resistors R1 and R2 and amplifies the faint voluntary myoelectric signal.

The multi-step amplifier 12 receives the voluntary myoelectric signal amplified by the instrumentation amplifier 11 and amplifies it to a level which the controller 13 can process.

The controller 13 receives the voluntary myoelectric signal amplified by the multi-step amplifier 12 and converts the analogue voltage to a digital signal, and thereafter the controller 13 calculates an amount of the voluntary myoelectric signal and controls the H-bridge circuit 10 (turning ON/OFF of the photoMOS relays SW1~SW4). By controlling the H-bridge circuit 10, timings of the stimulus pulses are controlled. For example, it controls the ON-timings of the stimulus pulses, durations of turning on (widths of the pulses) and cycles of the pulses.

The boost circuit 14 is a non-isolated boost circuit without a transformer and regularly supplies a direct current voltage of about +100V by boosting a voltage from the battery 17. Therefore, even if the stimulus is continuously output, an electrical potential does not drop, and so a stable stimulus output can be obtained.

The H-bridge circuit 10 consists of the photoMOS relays SW1, SW2, SW3 and SW4. The photoMOS relays SW1 and SW3 are connected serially, and the photoMOS relays SW2 and SW4 are connected serially. A common terminal of the photoMOS relays SW1 and SW2 is connected to a +100V terminal of the boost circuit 14, and a common terminal of the photoMOS relays SW3 and SW4 is connected to a ground terminal of the boost circuit 14. A common terminal of the photoMOS relays SW1 and SW3 is connected to the electrode E2, and a common terminal of the photoMOS relays SW2 and SW4 is connected to the electrode E1.

The photoMOS relays SW1 to SW4 are optically controlled and electrically isolated from the controller 13.

Figure 3:
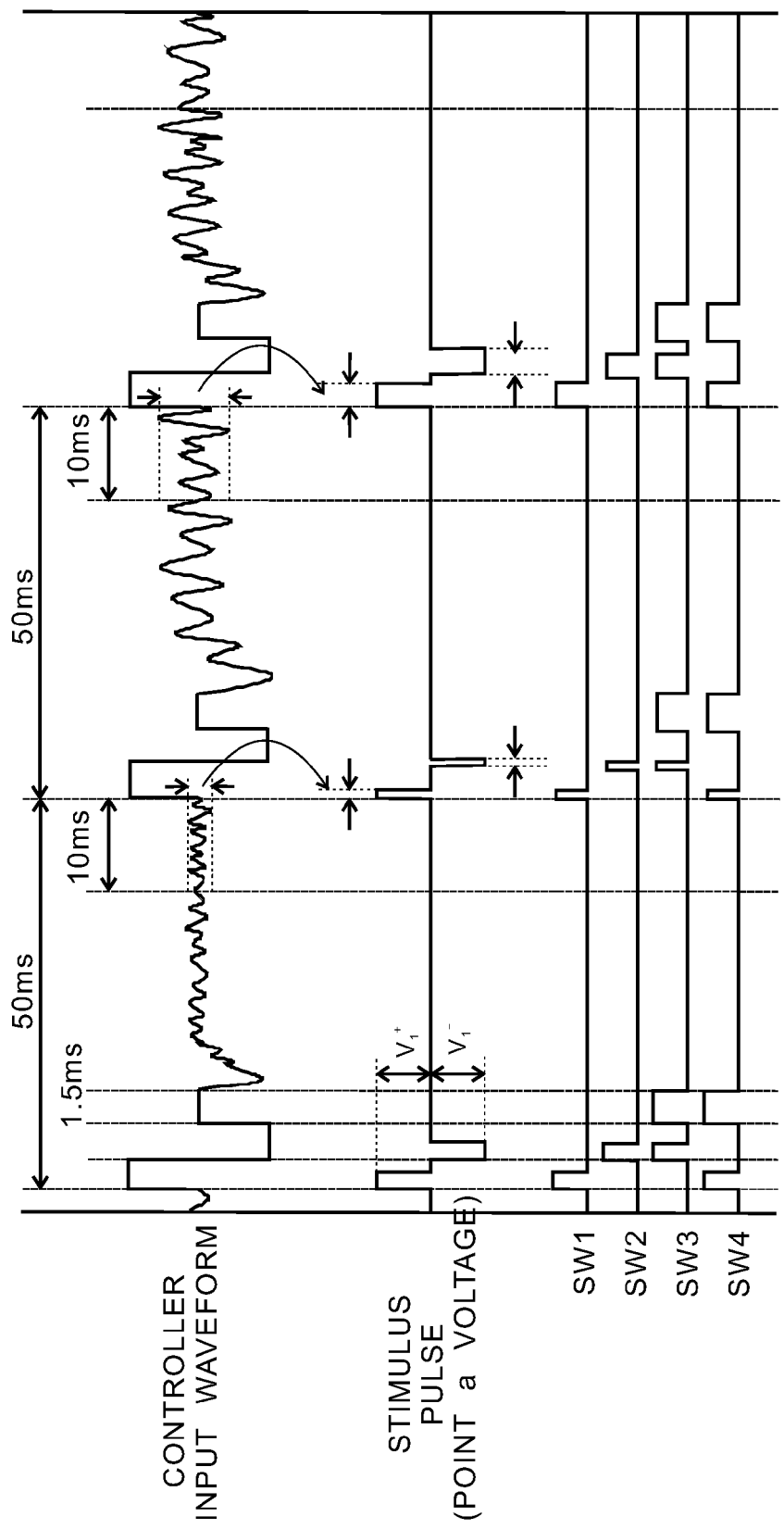
FIG. 3 is a waveform diagram for explaining an operation of the electrostimulator 1 according to the first embodiment of the present invention.

FIG. 3 is a waveform diagram for explaining an operation of the electrostimulator 1 according to the first embodiment of the present invention.

The stimulus pulse signal (a voltage at a point a in FIG. 1) is applied every 50 ms. A waveform of the stimulus pulse is realized by the photoMOS relays SW1 to SW4 controlled by the controller 13.

That is, the electrode E1 having a negative polarity is excited by flowing an electric current from the electrode E2 to the electrode E1 by turning on the photoMOS relays SW1 and SW4 while turning off the photoMOS relays SW2 and SW3, and thereafter the photoMOS relays SW1 and SW4 are turned off and then the photoMOS relays SW2 and SW3 are turned on to excite the electrode E2 having a negative polarity by flowing an electric current from the electrode E1 to the electrode E2 During that, the electrode E3 does not relate to the stimulus.

Thereafter, by turning on the switches SW3 and SW4 (or SW1 and SW2) for several milliseconds (1 to 1.5 ms), electric charges accumulated on the electrodes E1 and E2 are discharged to create equipotential so as to remove the artifact caused by the stimulus and to flatten and stabilize a baseline instantly.

Next, the voluntary myoelectric signal is detected in the last 10 ms of the 50 ms-cycle, and the pulse width of the stimulus pulse to be given in the next 50 ms-cycle is determined in accordance with the amplitude of the detected voluntary myoelectric signal. This operation is repeated every 50 ms.

As described in the above, by turning on the switches SW2 and SW4 at the same time, the artifact caused by the stimulus is removed, and the baseline is flattened and stabilized instantly. Therefore, the detection can be stably performed without performing the signal processing by the controller disclosed in the Patent Document 4 (Japanese Patent No. 396044).

Therefore, the maximum delay of the electric stimulus from generation of a myoelectric signal is shortened from conventional 120 ms to about 50 ms, which is shorter than a half of the conventional delay, and electric stimulus can be generated in accordance with actions even in case of fast walking actions.

Moreover, the stimulus pulse is not limited to a combination of one positive pulse and one negative pulse but may be arbitrary waveforms, for example, a combination of continuous positive-negative-positive-negative pulses, etc.

Furthermore, 1 to 1.5 ms is necessary for exciting the electrode E1 and also 1 to 1.5 ms is necessary for exciting the electrode E2, another 1 to 1.5 ms is necessary for simultaneously turning on the switches SW3 and SW4, and still another 10 ms is necessary for detecting the voluntary myoelectric signal. Therefore, the generation of the electric stimulus can be performed at a cycle of about 15 ms at the minimum although it is necessary to consider a biological reaction such as a refractory period just after the stimulus, suppression of voluntary muscle activities, etc.

Figure 4:
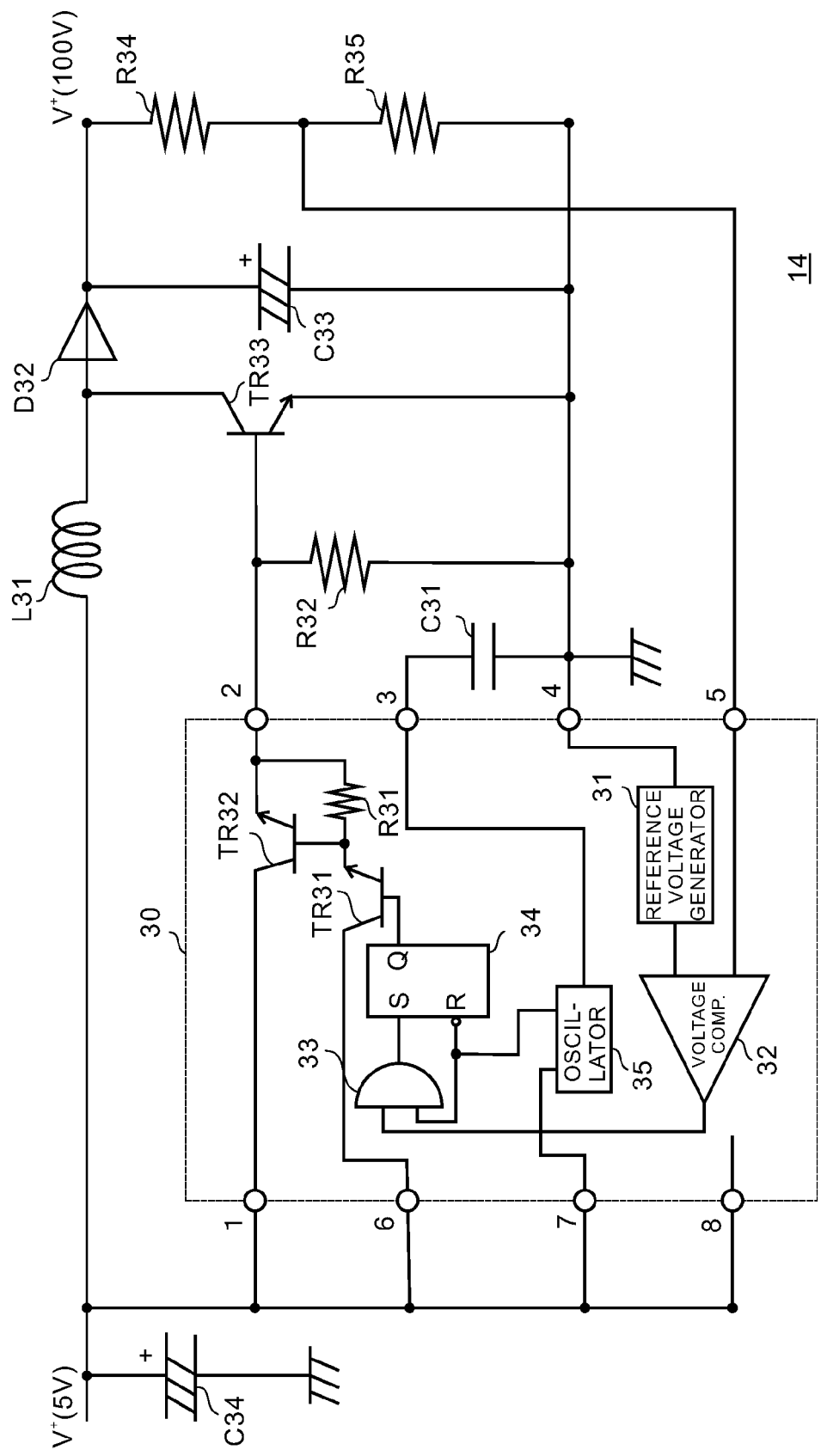
FIG. 4 is a circuit diagram showing a structure of the boost circuit 14.

FIG. 4 is a circuit diagram showing a structure of the boost circuit 14.

As described in the above, the boost circuit 14 is a DC-DC converter without a transformer, and more specifically it obtains a high voltage (+100V) by monitoring an output voltage with an IC 30 and accumulating electric charges with switching when the output voltage is not higher than a predetermined voltage.

First, the IC 30 is explained. A voltage comparator 32 compares a voltage of a terminal 5 with a reference voltage from a reference voltage generator 31 and outputs a high voltage to one terminal of an AND circuit 33 when the voltage of the terminal 5 is lower than the reference voltage.

On the other hand, an output of an oscillator 35 is supplied to another terminal of the AND circuit and input to an R-terminal of a set-reset flip-flop (FF) 34 after being inverted. An output of the AND circuit is input to an S-terminal of the FF 34.

An output Q of the FF 34 is input to a base of a transistor TR31, an emitter of the transistor TR31 is connected to a terminal 2 via a resistor R31 and input to a base of a transistor TR32, and an emitter of the transistor TR32 is connected to the terminal 2.

By that, the output Q of the FF 34 is repeatedly inverted at an oscillating frequency of the oscillator 35 when the voltage of the terminal 5 is lower than the reference voltage and electrically connects a terminal 1 and the terminal 2 periodically. When the voltage of the terminal 5 is higher than the reference voltage, the output of the AND circuit 33 remains low voltage, and so the output Q remains low voltage; therefore, the terminal 1 and the terminal 2 are not electrically connected.

When the terminal 1 and the terminal 2 are electrically connected, the power source voltage (+5V) is applied to a resistor R32 and input to a base of the transistor TR33 to turn on the transistor TR33. By that, an electrical current flows to a ground terminal 4 from the power source (+5V) via a coil L31.

Next, when the terminal 1 and the terminal 2 are electrically disconnected, the transistor TR33 is turned off, and the coil L31 flows the electric current to a capacitor C33 via a diode D32 to accumulate electric charges on the capacitor C33. By repeating this operation, the high voltage (+100V) can be obtained on the capacitor C33. The high voltage is divided by the resistor R34 and the resistor R35 and monitored at the terminal 5 by the IC 30. Moreover, the capacitor C34 maintains the power source voltage (+5V).

Figure 5:
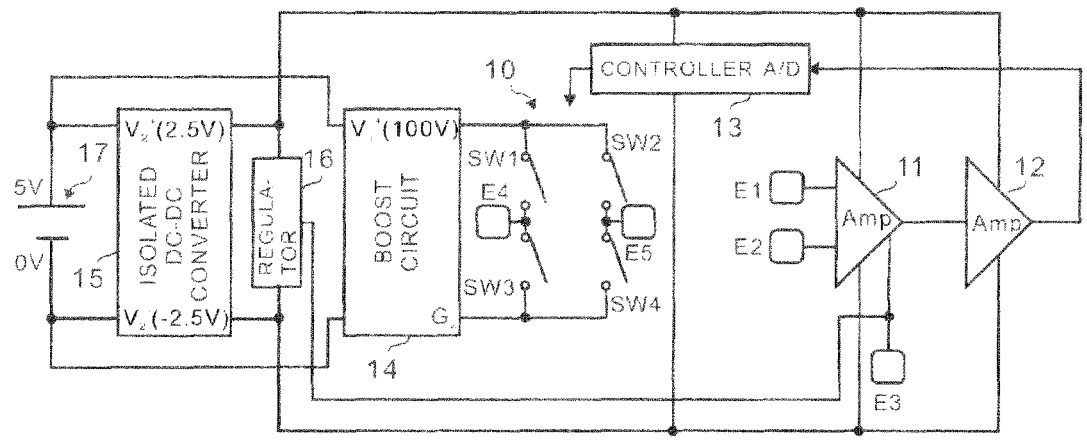
FIG. 5 is a circuit diagram showing a structure of an electrostimulator according to a second embodiment of the present invention.

FIG. 5 is a circuit diagram showing a structure of an electrostimulator 2 according to a second embodiment of the present invention.

The second embodiment is different from the first embodiment in that the electrodes E1 and E2 functions only as recording electrodes and electrodes E5 and E6 are added as stimulus electrodes. Other structures are similar to the first embodiment and so the explanations for those will be omitted.

In this embodiment also the stimulus is not applied to the electrode E3, and so stable output of the stimulus can be obtained by supplying the high voltage continuously.

In the second embodiment, the detection of the voluntary myoelectric signal and application of the electric stimulus can be performed on the different positions (on different muscles including muscles of other person). For example, in case of using the electrostimulator 2 according to this embodiment for a patient with facial nerve paralysis, the electrodes E1 and E2 can be disposed on a normal side to detect voluntary myoelectric signals, and the electrodes E4 and E5 can be disposed on a paralyzed side to give electric stimulus.

Figure 6:
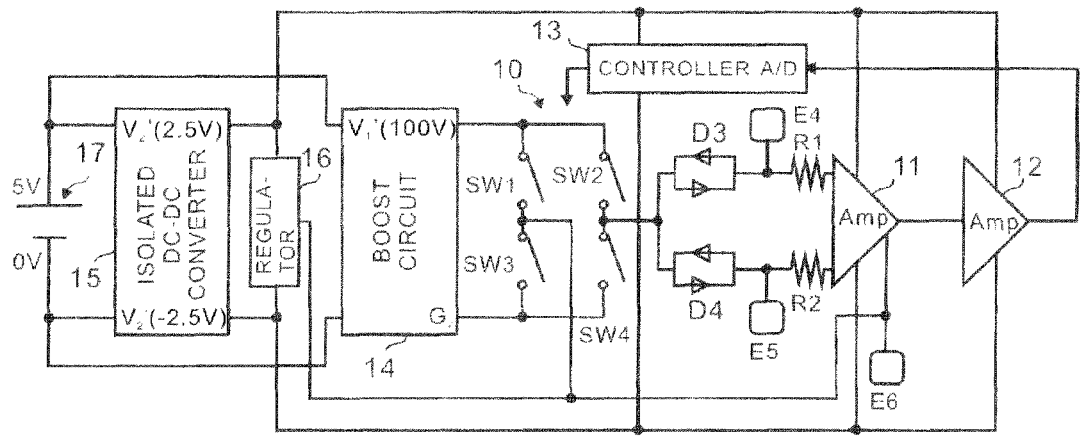
FIG. 6 is a circuit diagram showing a structure of an electrostimulator 3 according to a third embodiment of the present invention.

FIG. 6 is a circuit diagram showing a structure of an electrostimulator 3 according to a third embodiment of the present invention. The electrostimulator 3 according to the third embodiment is similar to the first embodiment in that a power is supplied to the controller 13 and the amplifiers 11 and 12 from the battery 17 via the isolated DC-DC converter 15, but electric current flows between the electrodes E4 and E5 and the electrode E6 in the third embodiment.

In the electrostimulator 3 according to the third embodiment, a diac D3 (fifth switch) is connected between the common terminal of the photoMOS relays SW2 and SW4 and the electrode E4, and a diac D4 (sixth switch) is connected between the common terminal of the photoMOS relays SW2 and SW4 and the electrode E5. Moreover, the electrode E6 disposed on a skin surface is connected to the common terminal of the photoMOS relays SW1 and SW3, to the reference terminal of the amplifier 11 and to the output terminal of the regulator 16. By using diacs for the fifth and sixth switches, the electrostimulator 3 is further miniaturized.

Figure 7:
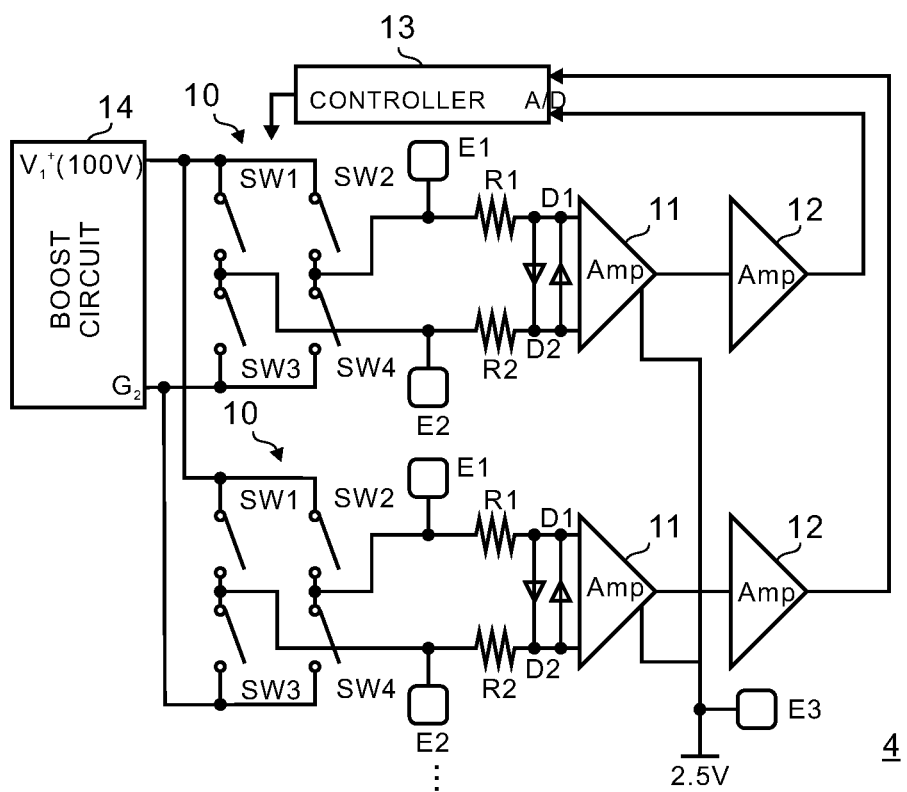
FIG. 7 is a circuit diagram showing a structure of an electrostimulator 4 according to a fourth embodiment of the present invention.
Figure 8:
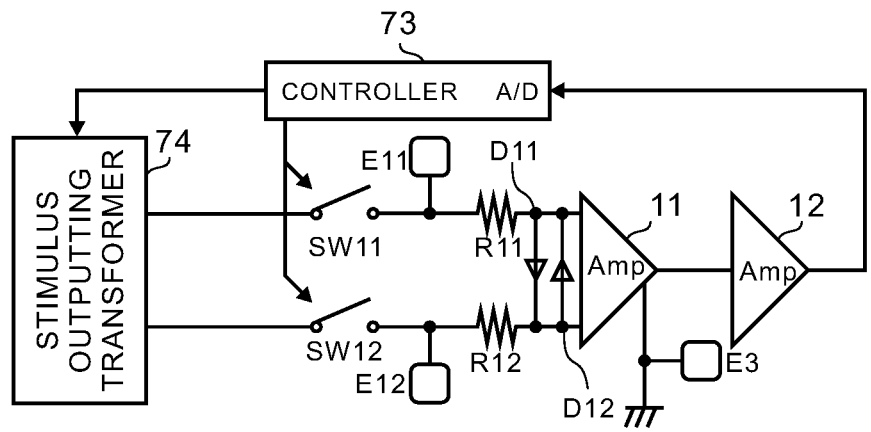
FIG. 8 is a circuit diagram showing a structure of an electrostimulator according to a first prior art.
Figure 9:
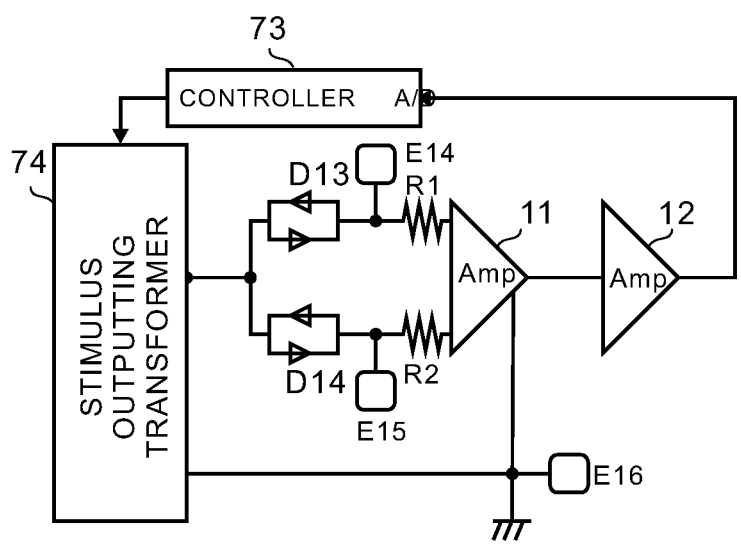
FIG. 9 is a circuit diagram showing a structure of an electrostimulator according to a second prior art.
Figure 10:
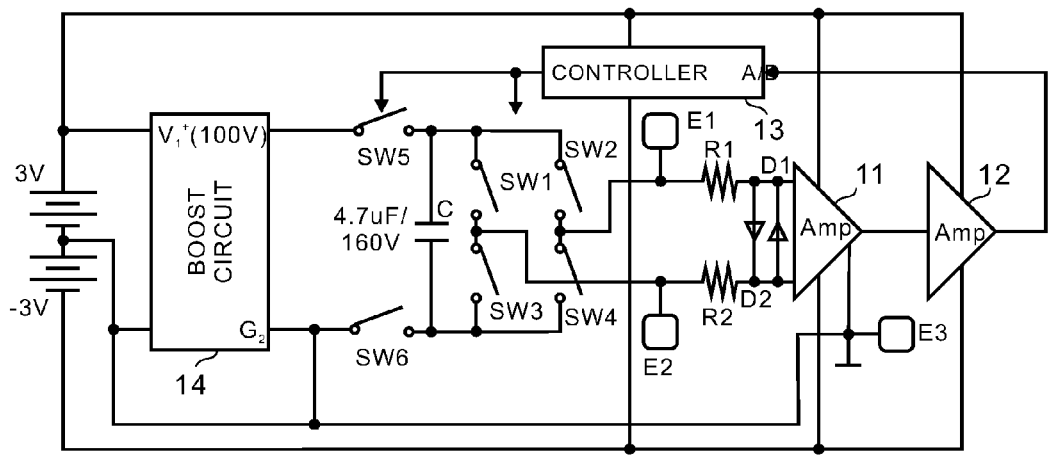
FIG. 10 is a circuit diagram showing a structure of an electrostimulator according to a third prior art.
Figure 11:
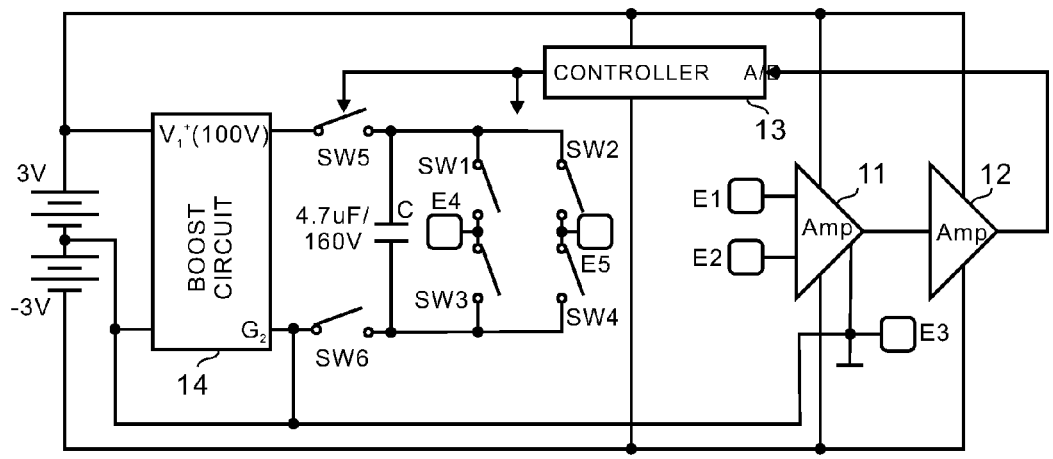
FIG. 11 is a circuit diagram showing a structure of an electrostimulator according to a first comparative example.

FIG. 7 is a circuit diagram showing a structure of an electrostimulator 4 according to a fourth embodiment of the present invention. The electrostimulator 4 according to this embodiment is able to give stimulus to a plurality of muscles by installing more H-bridge circuit(s) 10 and more myoelectric signal detection unit(s) (the electrodes E1 and E2, the protective resistors R1 and R2, the diodes D1 and D2, the instrumentation amplifier 11 and the multi-step amplifier 12). Moreover, by selecting a switch to be turned on, an electric current can be flown to an arbitrary channel in an arbitrary direction.

As described in the above, according to the embodiments of the present invention, a transformer-less output type myoelectric controlling electrostimulator can be driven by one battery, output stable electric stimulus and detect stable voluntary myoelectric signals by converging artifact caused by the stimulus.

According to the embodiments of the present invention, a voltage of about 100V for stimulus is generated from a 5V external battery for a mobile phone or the like by the non-isolated transformer-less boost circuit 14. Simultaneously a power source (about 5V) for the controller 13 and the amplifiers 11 and 12 is generated by the isolated DC-DC converter 15, and a mid-point voltage of the amplifier power source used as a reference voltage for the amplifiers 11 and 12 is generated by the regulator 16. The negative polarity electrode E1 is excited by flowing an electric current to the electrode E1 from the electrode E2 by turning on the photoMOS relays SW1 and SW4 while the photoMOS relays SW2 and SW3 remain turned off. Then, after turning off the photoMOS relays SW1 and SW4, the photoMOS relays SW2 and SW3 are turned on to excite the negative polarity electrode E2 by flowing an electrical current to the electrode E2 from the electrode E1. Thereafter, the switches SW 3 and SW4 are turned on for several milliseconds, and the following voluntary myoelectric signal is stably detected.

After outputting the stimulus pulse, the electrodes E1 and E2 are made to have the same electric potential by discharging electric charges accumulated thereon by turning on the switches SW3 and SW4 for several milliseconds, and so the following voluntary myoelectric signal can be stably detected without a signal process by the controller. Therefore, the maximum delay from generation of myoelectric signal to electric stimulus is shortened, and the electric stimulus can be generated even for a fast walking motion with following up the motion.

According to each embodiment of the present invention, a weak myoelectric signal can be detected from a muscle where a patient with stroke can slightly contract intentionally comparing to that in good health, and the muscle can be stimulated by applying the electric stimulus signal generated by amplifying the myoelectric signal.

Moreover, this stimulation of a muscle can assist a weak motion of a body part (for example, an arm, a leg, a finger, etc.) which a patient with stroke intends to move. As in the above, rehabilitation by using electric stimulus can be applied to 80 to 90% of patients with stroke as far as they can move by themselves.

Further, the electrostimulators according to the embodiments of the present invention can be applied to patients with facial nerve paralysis or with dysphagia. In case of the facial nerve paralysis, electric stimulus is given to a muscle on a paralyzed side in accordance with a myoelectric signal of the same muscle on a health side to reconstruct a symmetrical expression on a face. In case of assisting swallowing, electric stimulus is given to the group of suprahyoid muscles of a patient with insufficient swallowing function (laryngeal elevation) to promote sufficient laryngeal elevation.

The present invention has been described in connection with the preferred embodiments. The invention is not limited only to the above embodiments. It is apparent that various What are claimed are:

1. An electrostimulator, comprising:
a boost circuit with no transformer, which is configured to receive a power supply from a battery and outputs a stimulus signal;
a first electrode and a second electrode which are adapted to be disposed on a skin surface, detect a voluntary myoelectric signal from the skin surface, and provide the stimulus signal output from the boost circuit to the skin surface;
an amplification circuit which amplifies the voluntary myoelectric signal detected by the first and the second electrodes;
a controller which controls the stimulus signal in accordance with the voluntary myoelectric signal detected by the first and the second electrodes;
an H-bridge circuit which comprises a first switch and a third switch that are connected in series and have a common connection terminal that is connected to the second electrode, and a second switch and a fourth switch that are connected in series and have a common connection terminal that is connected to the first electrode, the first switch, the second switch, the third switch, and the fourth switch being connected in parallel, and the H-bridge circuit being controlled by the controller;
an isolated DC-DC converter which is configured to receive the power supply from the battery and supplies power to the controller and the amplification circuit;
a regulator which outputs a midpoint voltage of a power-supply voltage outputted by the DC-DC converter; and
a third electrode which is connected to the regulator and a reference terminal of the amplification circuit, and which is adapted to be disposed on the skin surface.

2. The electrostimulator according to claim 1, wherein the electrostimulator comprises a plurality of the H-bridge circuits and a plurality of voluntary myoelectric signal detection units each comprising a pair of the first and the second electrodes and the amplification circuit.

3. The electrostimulator according to claim 1, wherein the controller closes the third and the fourth switches or the first and the second switches for a predetermined time after the stimulus signal is provided to the skin surface.

4. The electrostimulator according to claim 1, wherein the controller controls a timing and a duration of providing the stimulus signal to the skin surface.

5. An electrostimulator, comprising:
a boost circuit with no transformer, which is configured to receive a power supply from a battery and outputs a stimulus signal;
a first electrode and a second electrode which are adapted to be disposed on a skin surface and detect a voluntary myoelectric signal from the skin surface;
an amplification circuit which amplifies the voluntary myoelectric signal detected by the first and the second electrodes;
a fourth electrode and a fifth electrode which are adapted to be disposed on the skin surface and provide the stimulus signal output from the boost circuit to the skin surface;
a controller which controls the stimulus signal in accordance with the voluntary myoelectric signal detected by the first and the second electrodes;
an H-bridge circuit which comprises a first switch and a third switch that are connected in series and have a common connection terminal that is connected to the fourth electrode, and a second switch and a fourth switch that are connected in series and have a common connection terminal that is connected to the fifth electrode, the first switch, the second switch, the third switch and the fourth switch being connected in parallel, and the H-bridge circuit being controlled by the controller;
an isolated DC-DC converter which is configured to receive the power supply from the battery and supplies power to the controller and the amplification circuit;
a regulator which outputs a midpoint voltage of a power-supply voltage outputted by the DC-DC converter; and
a third electrode which is connected to the regulator and a reference terminal of the amplification circuit, and which is adapted to be disposed on the skin surface.

6. The electrostimulator according to claim 5, wherein the electrostimulator comprises a plurality of the H-bridge circuits and a plurality of voluntary myoelectric signal detection units each comprising a pair of the first and the second electrodes and the amplification circuit.

7. The electrostimulator according to claim 5, wherein the controller closes the third and the fourth switches or the first and the second switches for a predetermined time after the stimulus signal is provided to the skin surface.

8. The electrostimulator according to claim 5, wherein the controller controls a timing and a duration of providing the stimulus signal to the skin surface.

9. An electrostimulator, comprising:
a boost circuit with no transformer, which is configured to receive a power supply from a battery and outputs a stimulus signal;
a first electrode and a second electrode which are adapted to be disposed on a skin surface, detect a voluntary myoelectric signal from the skin surface, and provide the stimulus signal output from the boost circuit to the skin surface;
an amplification circuit which amplifies the voluntary myoelectric signal detected by the first and the second electrodes;
a controller which controls the stimulus signal in accordance with the voluntary myoelectric signal detected by the first and the second electrodes;
an H-bridge circuit which comprises a first switch and a third switch that are connected in series and have a common connection terminal that is connected to the second electrode, and a second switch and a fourth switch that are connected in series and have a common connection terminal that is connected to the first electrode, the first switch, the second switch, the third switch and the fourth switch being connected in parallel, the H-bridge circuit being controlled by the controller;
a fifth switch which is connected between the common connection terminal of the second and the fourth switches and the first electrode;
a sixth switch which is connected between the common connection terminal of the second and the fourth switches and the second electrode;
an isolated DC-DC converter which is configured to receive the power supply from the battery and supplies a power to the controller and the amplification circuit; a regulator which outputs a midpoint voltage of a power-supply voltage outputted by the DC-DC converter; and
a third electrode which is connected to the common connection terminal of the first and the third switches, the regulator and a reference terminal of the amplification circuit, and which is adapted to be disposed on the skin surface.

10. The electrostimulator according to claim 9, wherein the fifth and the sixth switches are diodes for alternating current.

11. The electrostimulator according to claim 9, wherein the electrostimulator comprises a plurality of the H-bridge circuits and a plurality of voluntary myoelectric signal detection units each comprising a pair of the first and the second electrodes and the amplification circuit.

12. The electrostimulator according to claim 9, wherein the controller closes the third and the fourth switches or the first and the second switches for a predetermined time after the stimulus signal is provided to the skin surface.

13. The electrostimulator according to claim 9, wherein the controller controls a timing and a duration of providing the stimulus signal to the skin surface.

* * * * *